United States Patent [19]

Jacewicz

[11] Patent Number: 4,647,692

[45] Date of Patent: Mar. 3, 1987

[54] RACEMIZATION AND RESOLUTION OF α-AMINO ACIDS

[75] Inventor: Victor W. Jacewicz, Reigate, England

[73] Assignee: Beecham Group p.l.c., England

[21] Appl. No.: 770,508

[22] Filed: Aug. 28, 1985

[30] Foreign Application Priority Data

Aug. 30, 1985 [GB] United Kingdom ............... 8421964

[51] Int. Cl.⁴ .................. C07B 55/00; C07B 57/00
[52] U.S. Cl. ................................ 562/401; 562/444
[58] Field of Search ....................................... 562/401

[56] References Cited

U.S. PATENT DOCUMENTS 4,401,820  8/1983  Chibata et al. ............... 562/401 X

FOREIGN PATENT DOCUMENTS 0057092  8/1982  European Pat. Off. .
54-109912  8/1979  Japan .

Primary Examiner—Natalie Trousof
Assistant Examiner—Vera C. Clarke
Attorney, Agent, or Firm—Jacobs & Jacobs

[57] ABSTRACT

Process for racemization of amino acids by use of a ketone and an organic acid such as acetic acid. In particular, a process for resolution of free α-amino acids with in situ racemization. The resolution of 4-hydroxyphenylglycine and 3,4-dihydroxyphenylglycine with 3-bromocamphor-9-sulphonic acid with in situ racemization are specifically mentioned.

7 Claims, No Drawings

RACEMIZATION AND RESOLUTION OF α-AMINO ACIDS

This invention relates to a chemical process for the racemisation of α-amino acids.

Optically active α-amino acids are useful in the synthesis of many physiologically active compounds, in particular as side-chains in penicillin and cephalosporin antibiotics. It is convenient to synthesise α-amino acids in the racemic form and then resolve into the separate enantiomers. However, in most cases, only one enantiomer has commercial utility and it is therefore desirable to racemise the unwanted isomer, so that the racemate produced may again be subjected to resolution.

British Pat. No. 1,432,822 describes the racemisation of an ester of an amino acid by the use or an aldehyde or ketone. British Pat. No. 1,417,060 describes the racemisation of an N-acyl amino acid by heating in a solvent selected from phosphoric acid tri-esters, lower fatty acids containing up to 4 carbon atoms, dialkylformamides, ketones and dialkylsulphoxides. British Pat. No. 1,560,907 describes the racemisation of an amide of an amino acid by heating in solvent in the presence of a ketone and an acid having a dissociation constant below $1.8 \times 10^{-4}$. Japanese patent application No. 1512/78 (Kokai No. 54-109912) describes the racemisation of an ester of an amino acid by heating in the presence of a ketone and a protonic or Lewis acid. European patent specification No. 57092 describes the racemisation of an amino acid itself or a salt thereof in the presence of an aliphatic acid and an aldehyde.

The present invention relates to the racemisation of free amino acids by the use of a ketone. The above prior art teaches away from such a process.

Accordingly the present invention provides a process for racemisation of an α-amino acid which comprises treating an optically active α-amino acid with a ketone in the presence of an organic acid.

Suitable amino acids include naturally occurring neutral, acidic and basic α-amino acids. A preferrred class of amino acid are represented by formula (I):

wherein R represents an optionally substituted hydrocarbon or heterocyclic group.

The term 'hydrocarbon' includes groups having up to 18 carbon atoms, suitably up to 10 carbon atoms, conveniently up to 6 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)-alkyl, aryl, and aryl($C_{1-6}$)alkyl.

Preferably R is an aryl group.

Suitable alkyl groups include straight and branched chain alkyl groups containing from 1 to 6 carbon atoms, such as methyl, ethyl, propyl and butyl. A particular alkyl group is methyl.

The term 'heterocyclyl' includes single or fused rings comprising up to four hetero atoms in the ring selected from oxygen, nitrogen and sulphur and optionally substituted with up to three halogen, $C_{1-6}$ alkyl, $C_{1-6}$ alkoxy, halo-($C_{1-6}$)-alkyl, hydroxy, amino, carboxy, $C_{1-6}$ alkoxycarbonyl, $C_{1-6}$ alkoxycarbonyl($C_{1-6}$) alkyl, aryl or oxo groups.

Suitably the heterocyclic ring comprises from 4 to 7 ring atoms, preferably 5 to 6 atoms.

When used herein the term 'aryl' includes phenyl and naphthyl optionally substituted with up to five, preferably up to three, groups selected from halogen, $C_{1-6}$ alkyl, phenyl, $C_{1-6}$ alkoxy, halo($C_{1-6}$) alkyl, hydroxy, amino, nitro, carboxy, $C_{1-6}$ alkoxycarbonyl, $C_{1-6}$ alkoxycarbonyl-($C_{1-6}$)-alkyl $C_{1-6}$ alkylcarbonyloxy, or $C_{1-6}$ alkylcarbonyl groups.

Suitable optional substituents for the hydro-carbon, heterocyclic groups and organic radicals include $C_{1-6}$ alkyl, heterocyclic, amino, $C_{1-6}$ alkanoyl-amino, mono, di- and tri- ($C_{1-6}$) alkylamino, hydroxy, $C_{1-6}$ alkoxy, mercapto, $C_{1-6}$ alkylthio, heterocyclyl-thio, arylthio, sulphamoyl, carbamoyl, amidino, guanidino, nitro, chloro, bromo, fluoro, carboxy and salts and esters thereof, $C_{1-6}$ alkanoyloxy, aryl-carbonyl and heterocyclylcarbonyl.

Preferably R represents phenyl optionally substituted with up to three groups selected from hydroxy or halogen. Particularly preferred α-amino acids of formula (I) include phenylglycine, mono- and di-hydroxyphenyl glycines, especially 4-hydroxyphenyl glycine and 3,4-dihydroxyphenylglycine.

The α-amino acid may be employed in the form of the acid itself or a salt thereof.

Suitable salts of the α-amino acid include acid salts, basic salts, internal zwitterionic salts and acid addition salts. Preferred are alkali metal salts such as sodium, and acid addition salts such as acetate or benzoate. Most preferred are such salts which have been used in the resolution of the α-amino acid such as bromocamphor sulphonate salts.

Ketones which are suitable for the process of the invention may have the formula II:

$$R^1\text{-CO-}R^2 \qquad \text{II}$$

wherein $R^1$ and $R^2$ may be the same or different and each represents a hydrocarbon or heterocyclic group, as defined above, or $R^1$ and $R^2$ together complete a cycloalkanone ring.

Preferred ketones include acetone, methylethylketone, methylisobutylketone, cyclohexanone and cyclopentanone.

The ketone may be employed in excess. Conveniently the quantity of ketone employed is from 2% to 50% of the total solvent volume, i.e. 0.5 to 20 mole, preferably 1 to 10 mole per mole of α-amino acid.

Organic acids which are suitable for the process of the invention include $C_{1-6}$ alkanoic acids, for example formic acid, acetic acid, propionic acid and butyric acid. A preferred organic acid is acetic acid. It is preferred to use from 5 to 50 moles of organic acid per mole of amino acid. The organic acid, together with the ketone, may conveniently form the solvent for the racemisation process.

Excess of strong acids tends to inhibit the racemisation and is to be avoided although salts of strong acids may be used in the process.

The ketone and the organic acid employed in the process may conveniently be used as the solvent in the racemisation reaction. Additional co-solvents may, however, also be employed.

After the reaction the racemic amino acid may be recovered by conventional methods, for example by crystallisation.

Processes of the present invention are normally carried out at temperatures of 60° C. or more, preferably 80° C. or more. Most preferred are reactions carried out under reflux. Thus where acetic acid is used as the organic acid, the reaction is carried out at 115°-120° C. at atmospheric pressure or at about 70° C. under vacuum.

As stated above, the advantage of the process of the present invention is to provide a racemic α-amino acid which can be subjected to resolution in order to obtain further quantities of the desired enantiomer. In a further preferred embodiment of this invention, the racemisation process is carried out in the same solution as a resolution process, so that the unwanted isomer is racemised in situ while the desired isomer is continuously removed from solution by the resolving agent.

Accordingly, in a further aspect, the present invention provides a process for the preparation of an optically active α-amino acid, which process comprises resolving a racemic α-amino acid in the presence of a ketone and an organic acid.

The choice of resolving agent will depend, of course, on the particular amino acid. For example phenylglycine may be resolved using camphor-10-sulphonic acid; 4-hydroxyphenylglycine is conveniently resolved by using diastereoisomeric salts with 3-bromocamphor-9-sulphonic acid (which is also referred to as 3-bromocamphor-8-sulphonic acid - see Japanese application No. 50-148144; Kokai No. 52-71440). European patent application No. 85106310.7 discloses the resolution of 3,4 dihydroxyphenylglycine by using diastereoisomeric salts with 3-bromocamphor-9-sulphonic acid.

Thus, in a preferred embodiment, the present invention provides a process for the preparation of optically active 4-hydroxyphenylglycine or 3,4-dihydroxyphenylglycine, which process comprises allowing a 3-bromocamphor-9-sulphonate salt thereof to crystallise from a solution of a mixture of diastereoisomeric camphorsulphonate salts of a 4-hydroxyphenylglycine or 3,4 dihydroxyphenylglycine, in the presence of a ketone and an organic acid; and liberating said optically active 4-hydroxyphenylglycine or 3,4-dihydroxyphenylglycine.

In this way, preferential crystallisation of one of the enantiomers takes place and the remaining salt is racemised in situ.

The diastereoisomeric bromocamphorsulphonate salts are separated by preferential crystallisation.

Occasionally the crystallisation may need to be induced by concentration of the solution, by adding a further solvent in which one diastereoisomer is less soluble, such as water; or by seed crystals of the desired diastereoisomer. Such seeding may be particularly desirable for the salts of D-3,4-dihydroxyphenylglycine.

After isolation, the desired diastereoisomeric camphorsulphonate salt is treated with a base. Suitable bases are those which are capable of liberating the 4-hydroxyphenylglycine or 3,4 dihydroxyphenylglycine from the diastereoisomeric camphor sulphonate salt or, for example, bases which are stronger than the 4-hydroxyphenylglycine or 3,4 dihydroxyphenylglycine, such as sodium acetate, potassium acetate, sodium hydroxide and potassium hydroxide.

This salt-splitting reaction may, surprisingly, be carried out in virtually the same solvent system as the resolution and racemisation, normally the ketone and organic acid and in particular acetic acid, thus providing a significant advantage for the process of the invention over the prior art processes. However the presence of a little water, for example 5-10% is desirable to prevent racemisation occuring. This water is readily removed subsequently.

A further advantage for the process of the invention is the resistance of ketones to degradation. Thus whereas aldehydes rapidly degrade when the process is operated as a repeated cycle using the same solvent system, the process of the present invention can be operated more than 10 times in the same solvent without excessive ketone degradation. Moreover where the resolving agent is to be transferred out of the system by solvent extraction, the ketone may be used as the solvent for this extraction.

Yet a further advantage of the process of the present invention is that the liberated camphorsulphonic acid can readily be recovered and re-used.

The following Examples illustrate the present invention.

EXAMPLE 1

100 g aqueous solution containing 33.2 g 3-bromo-camphor-9-sulphonate potassium salt (KSC), 15.5 g potassium sulphate, 19 g concentrated sulphuric acid, and 150 ml methyl isobutyl ketone were stirred for 15 minutes and the phases separated. The aqueous phase was extracted with two further 50 ml portions of methyl isobutyl ketone and the combined organic phases clarified by filtration. The solvent was evaporated under vacuum, and the remaining solid (resolving agent free acid) was redissolved in 100 ml glacial acetic acid and 50 ml methyl isobutyl ketone and stirred with 15.8 g racemic 4-hydroxyphenyl glycine at 80° C. for 15 hours. At the end of this time the crystalline 4-hydroxyphenylglycine bromocamphor sulphonate was collected by filtration and found to contain 93:7 D(−)- to L(+)-4-hydroxyphenylglycine enatiomer ratio (92% yield).

41 g of the above salt was added in portions to 30 ml water maintained at 55° C. and the pH readjusted to 4.3 by addition of 45% w/w aqueous sodium hydroxide. After a further 0.5 hours at 55° C. the suspension was cooled to room temperature, the solid filtered, washed with water and dried to give 14 g D(−)-4-hydroxyphenylglycine (93% enantiomeric purity).

EXAMPLE 2

5 g L(+)4-hydroxyphenylglycine-3-bromocamphor-9-sulphonate (L(+)HSC) was heated at 90° C. together with 0.03 g sodium acetate, 13.3 ml glacial acetic acid, and 6.6 ml methyl isobutyl ketone for 48 hours. Hplc analysis showed that conversion to D(−)-4-hydroxyphenylglycine 3-bromocamphor-9-sulphonate (D(−)HSC) was in excess of 99%.

EXAMPLE 3

In a comparison of the catalytic activity of various ketones 1 g L(+)HSC was stirred in 5 ml glacial acetic acid at 80° C. for 1½ hours in the presence of 100 mg of various catalysts. The extent of the conversion L(+)HSC D(−)HSC is shown in the table below.

| methyl isobutyl ketone | 14% |
| cyclohexanone | 49% |
| acetone | 29% |
| mesitylene oxide | 14% |

| | |
|---|---|
| -continued | |
| butanone | 18% |

In similar experiments significant catalytic activity was also shown in cyclopentanone, cycloheptanone, phenylglyoxylic acid, and pyruvic acid.

EXAMPLE 4

50 g D(−)HSC, 15 ml H₂O, 15 ml butanone, 120 ml glacial acetic acid, and 19 g sodium acetate were stirred at 45° C. for 1 hour. The solid suspension was collected by filtration, washed with butanone and dried, and shown to be D(−)-4-hydroxyphenyl glycine completely free of resolving agent (14.4 g, 85% yield).

The above filtrate was mixed with racemic 4-hydroxyphenylglycine (12 g) and concentrated sulphuric acid (11.6 g). 150 ml solvent was removed by distillation and replaced by 200 ml glacial acetic acid and 20 ml butanone. The mixture was heated at 90° C. for two hours and when the reaction was found not to be proceeding satisfactorily, 0.2 g NaOH pellets were added to neutralise excess sulphuric acid. 15 hours heating at 90° C. gave a mixture of which the solid component was essentially enantiomerically pure.

To the above was added 9.4 g NaOH dissolved in 20 ml water and the mixture stirred for 1 hour at 45° C. This gave D(−)-4-hydroxyphenyglycine as a solid in suspension which was subsequently filtered washed and dried. Yield 11.67 g (97%), enantiomeric purity 97.3%.

EXAMPLE 5

500 g D(−)HSC, 550 ml glacial acetic acid, 200 ml butanone, 100 ml toluene, 100 ml water and 46 g NaOH in 50 ml water were stirred at 50° C. for 1 hour. The solid product was filtered off and washed with 180 ml glacial acetic acid and 20 ml butanone. Yield after drying—152.7 g, 87.4% D(−)-4-hydroxyphenylglycine.

To the combined solvent phases were added 148 g racemic 4-hydroxyphenylglycine and 57.6 g concentrated sulphuric acid and the mixture refluxed in a Dean and Stark apparatus to condense and separate two solvent phases. The lower water rich phase was set aside and the upper phase returned to the apparatus. When phase separation had ceased about 150 ml solvent was distilled off for later use. The mixture was then heated at 90° C. for 15 hours. 46.1 g sodium hydroxide was dissolved in the water rich phase and, after cooling, added to the main mixture while it was maintained at about 50° C. After 1 hour at 500° the product D(−)-4-hydroxyphenylglycine was collected by filtration and washed with the 150 ml distillate, and dried. Yield 117 g. The above sequence was repeated a further 5 times to give a product averaging 93% yield and better than 98% enantiomeric purity.

EXAMPLE 6

Racemisation of 3,4-dihydroxyphenylglycine

D(−) 3,4-dihydroxyphenylglycine bromocamphorsulphonate was prepared by adding 275 ml 2N sulphuric acid to a suspension of D(−)-3,4-dihydroxyphenylglycine (50 g) and ammonium bromocamphor-9-sulphonate (90 g) in water (100 ml). After thorough drying 9.5 g of the above salt was mixed with glacial acetic acid (100 ml), butanone (50 ml), and sodium acetate (0.3 g). The mixture was stirred and refluxed for one hour at which point it consisted of a clear orange solution. This was removed from the heater, 2 g of sodium acetate added, and allowed to cool to room temperature during which time a crystalline precipitate formed. The precipitate was filtered, washed with acetic acid and butanone and air-dried. The infra-red spectrum showed the absence of resolving agent (peak at 1740 cm$^{-1}$) but was unlike either standard racemic or optically active amino acid. Yield 0.85 g (23%).

After recrystallisation of a small portion (0.4 g in 2 ml H₂O dissolved with 2 ml 2N HCl then precipitated with 2 ml 2N NaOH), filtering, washing, and drying, the product had an infra-red spectrum identical to standard racemic 3,4-dihydroxyphenylglycine.

EXAMPLE 7

Transformation of dextrorotatory to laevorotatory 3,4-dihydroxyphenylglycine.

4 g L(+)-3,4-dihydroxyphenylglycine ($\alpha_D^{20}$ 1% in 2N HCl= +149°) was added to crude bromocamphor-9-sulphonic acid (9.5 g=approx 1 equivalent), 30 ml glacial acetic acid, 10 ml butanone, 0.3 g sodium acetate, and heated to reflux to give a clear, dark brown solution. After several hours at reflux a precipitate began to form. This was collected, washed and dried and found to weigh 0.9 g. Heating of the residual solution was continued for 16 hours at Ca. 90° C. A second crop weighing 4.0 g was obtained in a similar manner to before. The infra-red spectrum was found to be identical to authentic D(−)-3,4-dihydroxyphenylglycine bromocamphorsulphonate. Total yield 45.4%.

3.5 g of the above salt was suspended in 20 ml H₂O treated with 2N NaOH to pH 4.1, and the resulting precipitate stirred at room temperature for 20 minutes. The product was then filtered, washed with water, and acetone and vacuum dried. Yield 1.13 g (87%). Infra-red spectrum identical to authentic D(−)-3,4-dihydroxyphenylglycine. $\alpha_D^{20}$ 1% in 2N HCl= −149°.

EXAMPLE 8

ISR Resolution of Racemic 3,4-dihydroxyphenylglycine.

Resolution

An evaporated methyl isobutyl ketone extract containing bromocamphorsulphonic acid (unknown purity, 168.5 g crude) was dissolved in glacial acetic acid (250 ml) and butanone (100 ml) at 80° C..

Racemic 3,4-dihydroxyphenylglycine monohydrate (52 g, assay 88.47%) was added and stirred vigorously. The amino acid went briefly into solution then crystallised as the bromocamphor-9-sulphonate salt. After half an hour this was filtered, washed with a minimum of glacial acetic acid and then butanone, dried and assayed. The procedure was repeated with two further additions of 20 g racemic acid. The third crop appeared to be a mixture (by IR spectrum) so an equivalence point had evidently been reached. A further small quantity of salt was obtained on standing at room temperature. Crops 1,2 and 4 represent a conventional resolution with a yield of salt of about 42% (uncorrected for purity).

In-Situ Racemisation

Toluene (100 ml) and sodium acetate (0.5 g) were added to the combined filtrate and washings and the solution refluxed gently with a cooled Dean and Stark head to remove a water rich lower phase.

After 5 hours lower phase separation had virtually ceased and a thick precipitate formed. The temperature was reduced to 70°–80° for 3 hours and the precipitate collected as above (crop 5). The filtrate was heated at 70°–80° overnight (Ca. 16 hours) and a sixth crop of solid salt obtained.

| Crop | IR | $\alpha_D^{20}$ [2%, H$_2$O] | Weight | Amino acid assay |
|---|---|---|---|---|
| 1 | salt | +11.9° | 47.8 g | — |
| 2 | salt | +12.7° | 27.6 g | — |
| 3 | mixture | — | 17.15 g | 65.1% |
| 4 | salt | +11.8° | 4.76 g | — |
| 5 | salt | +10.3° | 68.3 g | — |
| 6 | salt | +9.4° | 22.82 g | — |

Salt split

Crops 1,2,4,5 and 6 were suspended in 250 ml H$_2$O and treated with 50% aqueous NaOH to pH 4.5. After 1 hour stirring the product was filtered, washed with water, and dried.

Weight yield 58.56 g ($\alpha_D^{20}$ 1% in 2N HCl = −149°). Purity assay by hplc = 100.4%).

Yield (corrected for purity and ignoring crop 3) = 83.7%.

I claim:

1. A process for the racemisation of an α-amino acid of formula (I)

$$R-\underset{NH_2}{\underset{|}{CH}}-CO_2H \qquad (I)$$

wherein R represents phenyl optionally substituted with up to three hydroxy or halogen groups which comprises treating an optically active α-amino acid of formula (I) with a ketone of formula (II)

$$R^1\text{-CO-}R^2 \qquad (II)$$

wherein R$^1$ and R$^2$ are the same or different and each represents a hydrocarbon or heterocyclyl group or R$^1$ and R$^2$ together complete a cycloalkanone ring, in the presence of a C$_{1-6}$ alkanoic acid.

2. A process according to claim 1 in which the α-amino acid is phenylglycine, 4-hydroxyphenylglycine or 3,4-dihydroxyphenylglycine.

3. A process according to claim 1 in which the ketone is present at 0.5 to 20 mole per mole of α-amino acid and the C$_{1-6}$ alkanoic acid at from 5 to 50 mole per mole of α-amino acid.

4. A process for the preparation of an optically active α-amino acid of formula (I)

$$R-\underset{NH_2}{\underset{|}{CH}}-CO_2H \qquad (I)$$

wherein R represents phenyl optionally substituted with up to three hydroxy or halogen groups which comprises treating a racemic α-amino acid of formula (I) with 3-bromocamphor-9-sulphonic-acid in the presence of a ketone of formula (II)

$$R^1\text{-CO-}R^2 \qquad (II)$$

wherein R$^1$ and R$^2$ are the same or different and each represents a hydrocarbon or heterocyclyl group or R$^1$ and R$^2$ together complete a cycloalkanone ring, and a C$_{1-6}$ alkanoic acid.

5. A process according to claim 4 in which the α-amino acid is 4-hydroxyphenylglycine.

6. A process for the preparation of optically active 4-hydroxyphenylglycine or 3,4-dihydroxyphenylglycine which process comprises allowing a 3-bromocamphor-9-sulphonate salt thereof to crystallise from a solution of a mixture of the diastereoisomeric camphorsulphonate salts of 4-hydroxyphenylglycine or 3,4-dihyroxyphenylglycine in the presence of a ketone selected from the group consisting of acetone, methylethlketone, methylisobutyl ketone, cyclohexanone and cyclopentanone, and a C$_{1-6}$ alkanoic acid, said selected ketone and alkanoic acid serving as a solvent for the process, and liberating said optically active 4-hydroxyphenyglycine or 3,4-dihydroxyphenylglycine therefrom.

7. A process according to claim 6 in which the diastereoisomeric camphorsulphonate salt is treated with water and a base in the presence of the said selected ketone and alkanoic acid solvent.

* * * * *